United States Patent [19]

Ayache et al.

[11] Patent Number: 5,080,903

[45] Date of Patent: Jan. 14, 1992

[54] GALENICAL FORMS OF BETA-2-MIMETICS FOR ADMINISTRATION PERLINGUALLY AND SUBLINGUALLY

[75] Inventors: Josiane Ayache; Jean-Jacques Ayache; Georges Bruttmann, all of Grenoble; Patrick Pedrali, Annecy, all of France; Serge Robert, Braine le Chateau, Belgium

[73] Assignee: Societe Civile dite: "Medibrevex", Grenoble, France

[21] Appl. No.: 587,592

[22] Filed: Sep. 24, 1990

Related U.S. Application Data

[63] Continuation of Ser. No. 239,828, Sep. 2, 1988, abandoned.

[30] Foreign Application Priority Data

Sep. 2, 1987 [FR] France .............................. 87 12708

[51] Int. Cl.$^5$ .................... A61K 9/14; A61K 9/20; A61K 9/28; A61K 9/48
[52] U.S. Cl. .................... 424/433; 424/465; 424/474; 424/488; 424/451
[58] Field of Search ............... 424/474, 484, 488, 465

[56] References Cited

U.S. PATENT DOCUMENTS

| | | | |
|---|---|---|---|
| 3,975,391 | 8/1976 | Nakagawa et al. | 514/826 |
| 4,059,686 | 11/1977 | Tanaka et al. | 424/19 |
| 4,226,848 | 10/1980 | Nagai et al. | 424/488 |
| 4,707,497 | 11/1987 | Cecchi et al. | 514/647 |
| 4,751,071 | 6/1988 | Magruder et al. | 424/467 |
| 4,777,049 | 10/1988 | Magruder et al. | 424/457 |

FOREIGN PATENT DOCUMENTS

| | | |
|---|---|---|
| 0205282 | 12/1986 | European Pat. Off. |
| 2285896 | 9/1974 | France |
| 156609 | 8/1932 | Switzerland |

OTHER PUBLICATIONS

M. Traisnel et al.: "Galenica", vol. 16, "Medicaments Homeopathiques", 2nd edition, 1986, pp. 77-99.

*Primary Examiner*—Thurman K. Page
*Assistant Examiner*—Carlos Azpuru
*Attorney, Agent, or Firm*—Browdy & Neimark

[57] ABSTRACT

New galenical forms for administering beta-2-mimetics comprising a support conditioned to be placed into the sublingual and perlingual cavity of the mouth, the support made of a pharmaceutically acceptable compound which disintegrates under the action of saliva and progressively releases a controlled amount of the beta-2-mimetics into the sublingual and perlingual cavity of the mouth.

6 Claims, No Drawings

GALENICAL FORMS OF BETA-2-MIMETICS FOR ADMINISTRATION PERLINGUALLY AND SUBLINGUALLY

This application is a continuation of application Ser. No. 07/239,828, filed Sept. 2, 1988 now abandoned.

FIELD OF THE INVENTION

This invention relates to new galenical forms of beta-2-mimetics for administration perlingually and sublingually.

BACKGROUND OF THE INVENTION

The great importance offered by the present use of bronchodilators in certain dyspneic respiratory diseases such as asthma, chronic bronchitis and emphysema is known.

Beta-2-mimetics hold an important place among bronchodilators.

In 1948 ALQUIST discovered the existence of receptors that react differently to catecholamines; he described alpha receptors, vectors of exciting reactions and beta receptors, receptors of inhibiting reactions.

In 1967 LANDS differentiated these receptors into beta 1 and beta 2, the beta 1's serving for stimulation of the heart and fatty tissues, the beta 2's serving for relaxing of the bronchial vascular and uterine smooth muscles.

Following this discovery, selective beta 2 medicines (therefore specific of receptors of the same name) were put on the market and their main use was for treatment of asthma.

The bronchodilating activity of the products was shown by the improvement of the forced expiratory volume in 1 second ($FEV_1$) recorded by spirography.

The clinical activity and use of beta-2-mimetics are well known.

Beta-2-mimetics now exist in various galenical forms permitting their administration:
  orally: syrups and tables,
  by injection,
  by dosing aerosols.

Beta-2-mimetics are active orally but their effects appear only about two hours after their administration. Further, they are inactivated in the digestive tract and by the liver.

The effects are observed more rapidly by injection (subcutaneous or intravenous).

Use in the form of aerosols in undoubtedly the best, provided that the air passages are not congested and the use of the dosing aerosol by the patient is as perfect as possible. Now, few patients correctly use the apparatus made available to them, which frequently ends in abuse of the medicine, because the patient increases the dose, having the impression that one or two puffs are ineffective. Moreover, it is not certain that an aerosol puff reaches the peripheral passages. As already stressed in the case of patients having an active attack of asthmatic disease with bronchial obstruction (aggravated by an infection or by bronchial hypersecretion), it is risky to expect beneficial effects from this aerosol.

SUMMARY OF THE INVENTION

The inventors found that it was possible to administer the beta-2-mimetics perlingually and sublingually and that these new galenical forms had surprising advantages in comparison with existing galenical forms.

This perlingual and sublingual method is used because of its anatomic configuration which forms an entity in conjunction with other elements of the buccal cavity.

Diagrammatically, the sublingual region can be described in the following way (each of the constitutive elements having useful properties in the administration of medicines introduced in this way).

Overall, the sublingual region comprises:
  the lower face of the tongue which serves as a ceiling, which is very rich in blood vessels: veins, arteries and lymphatic vessels;
  the floor of the mouth which constitutes the lower part of the sublingual region. It is also an anatomic region which comprises many blood vessels and especially a very rich venous network, with arteries and lymphatic vessels;
  the edges of the sublingual region are formed by the ascending parts of the inferior maxilla, the gums and teeth.

In the floor of the mouth are salivary glands, sublingual glands, which secrete saliva as soon as there is a contact with the sublingual region. By its composition, saliva actively participates in the disintegration of the active pharmacological product present in this particular galenical form according to the invention.

Further, the histological structure shows the existence of immunocompetent cells in great number which, in some cases, will favor medicinal activity.

In comparison with the other constituents of the mouth: The area including the inside of the cheeks, the upper part of the tongue, and the sublingual region therefore appears as a particular anatomic entity which makes it a preferred way of administration of medicine in comparison with administration of medicines by injection.

All other medicines whose decomposition occurs in the mouth are necessarily swallowed.

In the sublingual galenical form according to the invention, the activity of the product is based on its possibility of rapid absorption without swallowing. The advantage offered by this galenical form in comparison with other galenical forms used inside the buccal cavity is that the product goes directly into the blood, which avoids hepatic metabolism; the product therefore acts faster with maximum effectiveness.

The galenical forms of beta-2-mimetics according to the invention are characterized in that the beta-2-mimetic is contained, in strictly controlled and reproducible amounts, in solid supports provided for a progressive release of the active ingredient perlingually and sublingually.

The advantages of the perlingual and sublingual galenical forms are numerous:
  the sublingual passage is fast: it does not require either dosing aerosol or injection equipment. Of course, this galenical forms is indicated only for bronchodilating treatments of ambulatory patients and, in no case, for patients whose clinical state arises from a hospitalization or very serious asthma;
  the galenical presentation makes it possible to have a strict dosage without risk of abuse (prescribed doses are limited by prescription);
  the effectiveness is preserved, even if there is bronchial congestion, since the passage takes place by the sublingual and perlingual vascular network.

DETAILED DESCRIPTION OF THE INVENTION

The process of obtaining new galenical forms according to the invention will now be disclosed in detail.

The starting product is salbutamol sulfate which can be obtained in a concentration of 0.1 mg per ml, for example, or even in other concentrations.

The starting product is lyophilized.

The lyophilized product obtained is put in solution in any suitable solvent, to obtain a mother solution. The solution used can be water or physiological serum; it can also be selected from other solvents, preferably polar solvents, such as low strength ethyl alcohol.

In case of dilutions of the mother solution, every precaution is taken to see that the amount of solvent remains constant, to achieve all impregnations in an identical way.

Then there is performed, in a turbine, with an injector of the "spray doser" type, the impregnation, with each of the dilutions, of the globules constituted in a way known in the art by a pharmaceutically acceptable solid support and especially of a saccharose-lactose mixture. It is obvious that, without going outside the scope of the invention, these globules could be replaced by powders or tablets, also adapted to perlingual and sublingual application.

The impregnation technique is that of multi-impregnation or fractionated impregnation to guarantee a perfect distribution of the homogeneous active principle.

Between each impregnation, drying is performed at a temperature less than or equal to 30° C. by passage of forced air dried in a chamber where a partial vacuum prevails obtained by the difference of the flow existing between this passage of air and a powerful suction apparatus.

The last impregnation is a protective impregnation of the "coating" type.

To guarantee that the physical and chemical integrity of the active principle will be maintained completely, the various impregnation stages are advantageously performed under a nitrogen atmosphere.

The last operation consists in putting the globules thus obtained into capsules, or optionally in placing said globules or powders or tablets in dosage tubes and finishing with the standard packaging (blisters for the capsules, boxes for the dose tubes).

Various types of treatment can be envisaged:

daily treatment: taking of two to four perlingual doses to be adapted to the spirography and clinical symptoms;

occasional treatment: taking of two to four capsules during a crisis, to be repeated until respiratory "recovery."

The clinical results are very surprising in comparison with aerosols and oral forms.

Another quite surprising advantage is the rapidity of action of the new galenical forms according to the invention which will allow the patient to reduce the daily dosage quickly; the patient no longer needs nursing assistance (subcutaneous injections). Only medical monitoring, dictated by the respiratory condition of the patient, remains necessary.

It is obvious that this invention cannot be limited to the concentrations, modes of fractionating or dilutions given above by way of nonlimiting example; these concentrations can, of course, be adapted to requirements; also the saccharose-lactose support can be replaced by another pharmaceutically acceptable support.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A method for administering beta-2-mimetics sublingually or perlingually comprising introducing into the sublingual or perlingual cavity of the mouth, a pharmaceutical composition comprising an effective amount of a beta-2-mimetic in a solid support which disintegrates rapidly under the action of saliva and progressively releases a controlled amount of said beta-2-mimetic into the sublingual or perlingual cavity of the mouth, and retaining said pharmaceutical composition in place in said sublingual or perlingual cavity until the composition has decomposed in the mouth.

2. The method according to claim 1 wherein said beta-2-mimetic is salbutamol sulfate.

3. A method for treating a patient suffering from a dyspneic respiratory disease by administering a beta-2-mimetic sublingually or perlingually comprising introducing into the sublingual or perlingual cavity of the mouth of said patient, a pharmaceutical composition comprising an effective amount of a beta-2-mimetic in a solid support which disintegrates rapidly under the action of saliva and progressively releases a controlled amount of said beta-2-mimetic into the sublingual and perlingual cavity of the mouth, and retaining said pharmaceutical composition in place in said sublingual or perlingual cavity until the composition has decomposed in the mouth.

4. The method according to claim 3 wherein said beta-2-mimetic is salbutamol sulfate.

5. The method according to claim 3 wherein said support is in divided form.

6. The method according to claim 3 wherein said support comprises a mixture of saccharose and lactose.

* * * * *